(12) United States Patent
Kauffmann et al.

(10) Patent No.: US 11,850,583 B2
(45) Date of Patent: Dec. 26, 2023

(54) PLASMA SEPARATION AND SAMPLE METERING DEVICE AND KITS AND METHODS OF USE RELATED THERETO

(71) Applicant: Siemens Healthcare Diagnostics Inc., Tarrytown, NY (US)

(72) Inventors: Aaron Kauffmann, Elkhart, IN (US); David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/617,881

(22) PCT Filed: Jun. 5, 2020

(86) PCT No.: PCT/US2020/036321
§ 371 (c)(1),
(2) Date: Dec. 9, 2021

(87) PCT Pub. No.: WO2020/251849
PCT Pub. Date: Dec. 17, 2020

(65) Prior Publication Data
US 2022/0266241 A1    Aug. 25, 2022

Related U.S. Application Data

(60) Provisional application No. 62/860,507, filed on Jun. 12, 2019.

(51) Int. Cl.
*B01L 3/00*        (2006.01)
(52) U.S. Cl.
CPC ....... *B01L 3/502* (2013.01); *B01L 2200/0605* (2013.01); *B01L 2400/0406* (2013.01)

(58) Field of Classification Search
CPC ............ B01L 3/502; B01L 2200/0605; B01L 2400/0406
USPC ........................................ 73/864.72
See application file for complete search history.

(56) References Cited

U.S. PATENT DOCUMENTS

| | | | | |
|---|---|---|---|---|
| 5,411,858 A | * | 5/1995 | McGeehan | B01L 3/5023 436/805 |
| 5,558,834 A | * | 9/1996 | Chu | G01N 33/525 436/66 |
| 2005/0106756 A1 | * | 5/2005 | Blankenstein | G01N 1/4077 436/523 |
| 2005/0130294 A1 | | 6/2005 | Randall et al. | |
| 2009/0120865 A1 | | 5/2009 | Chung et al. | |
| 2012/0024788 A1 | | 2/2012 | Kelso et al. | |

(Continued)

FOREIGN PATENT DOCUMENTS

EP    0832430 A1    4/1998
EP    1896851 A1    3/2008

(Continued)

OTHER PUBLICATIONS

International Search Report and Written Opinion of International Application No. PCT/US2020/036321 dated Sep. 9, 2020.

(Continued)

*Primary Examiner* — Benjamin R Whatley
*Assistant Examiner* — Jacqueline Brazin

(57) ABSTRACT

Devices, kits, and methods separating and metering a plasma sample from a patient's liquid test sample.

29 Claims, 5 Drawing Sheets

(56) References Cited

U.S. PATENT DOCUMENTS

| | | | |
|---|---|---|---|
| 2016/0029936 A1* | 2/2016 | Kvam | A61B 5/150022 |
| | | | 600/583 |
| 2017/0248618 A1 | 8/2017 | Baxter et al. | |
| 2019/0374938 A1* | 12/2019 | Shi | G01N 1/4005 |

FOREIGN PATENT DOCUMENTS

| | | |
|---|---|---|
| WO | 2006068027 A1 | 6/2009 |
| WO | 2015191450 A1 | 12/2015 |
| WO | 2016025726 A1 | 2/2016 |
| WO | 2018009384 A1 | 1/2018 |
| WO | 2019241384 A1 | 12/2019 |

OTHER PUBLICATIONS

Liu et al., "Membrane-Based, Sedimentation-Assisted Plasma Separator for Point-of-Care Applications", Oct. 5, 2013, Analytical Chemistry 85(21), pp. 10463-10470 (1-17).

* cited by examiner

PLASMA SEPARATION AND SAMPLE METERING DEVICE AND KITS AND METHODS OF USE RELATED THERETO

CROSS REFERENCE TO RELATED APPLICATIONS

This application claims benefit under 35 USC § 119(e) of U.S. Ser. No. 62/860,507, filed Jun. 12, 2019. The entire contents of the above-referenced patent application(s) are hereby expressly incorporated herein by reference.

STATEMENT REGARDING FEDERALLY FUNDED RESEARCH OR DEVELOPMENT

Not Applicable.

TECHNICAL FIELD

The presently disclosed and/or claimed inventive concept(s) relate to a device(s), kit(s), and method(s) for separating and/or metering a plasma sample for use in analyte(s) detection assays. More specifically, the presently disclosed and/or claimed inventive concept(s) relate to an improved device for separating, metering, and/or delivering a plasma sample obtained from a patient's whole blood sample for use in analyte(s) detection assays, as well as kits and methods of use related thereto.

BACKGROUND

Numerous devices, kits, and methods exist for injecting liquid test samples within a reaction vessel for conducting assays that detect analytes that may be present in the liquid test samples. Such devices have been proven to be effective in diagnostic assays that detect the presence and quantity of certain analytes indicative of a patient's health.

Hemolysis, as used herein, refers to the destruction, dissolution, or rupturing of red blood cells (RBCs) which results in the release of hemoglobin into the surrounding fluid(s). When a patient's liquid test sample is a whole blood sample, the hemoglobin is released into the surrounding plasma. The occurrence of a particular analyte(s) present in a patient's plasma sample may be indicative of a patient's medical condition or the mishandling of a sample, for instance, by a laboratory technician.

The separation of plasma has historically been accomplished through the centrifugation of a patient's whole blood sample which generates plasma which then may be interrogated (either optically or electrochemically) for the detection of hemolyzed hemoglobin. While accurate, this process is time consuming, requires additional instrumentation, and is inefficient for point-of-care (POC) applications. Accordingly, there is a current need for an integrated, improved plasma separation and sample metering device that is able to separate and meter a patient's extracted plasma sample for use in at least one analyte(s) detection and/or diagnostic assay. It is to such devices, kits, and methods that the presently disclosed and/or claimed inventive concept(s) is directed.

DETAILED DESCRIPTION

Figure 1A:
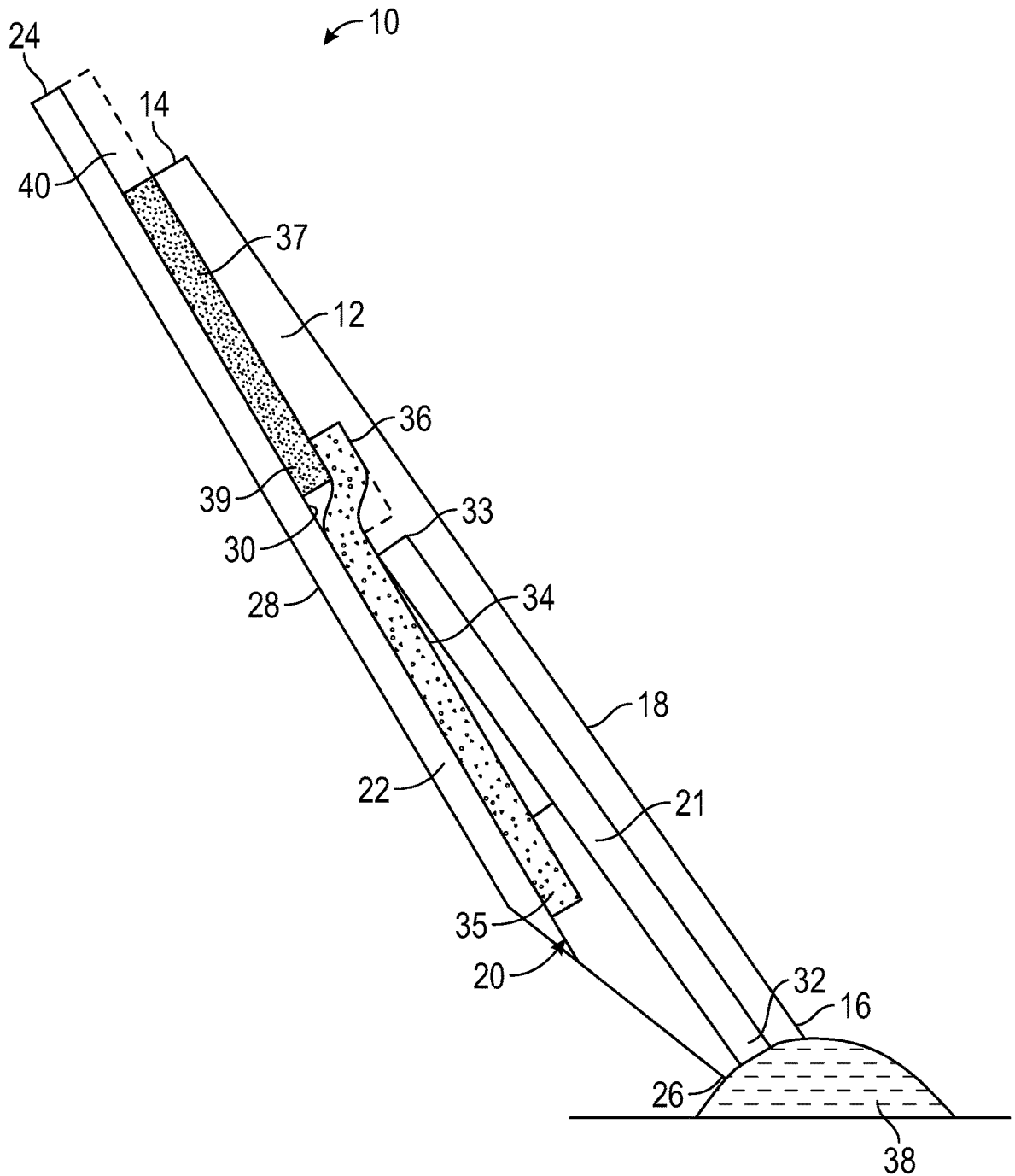
FIG. 1A is a side view of one non-limiting embodiment of the improved sample device constructed in accordance with the presently disclosed and/or claimed inventive concept(s) which is placed in a collection position for the collection of a patient's liquid test sample.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and/or claimed herein can be made and executed without undue experimentation in light of the present disclosure. While the compositions and methods of this presently disclosed and/or claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and/or claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperitoneal fluid, cystic fluid, sweat, interstitial fluid, tears, mucus, urine, bladder wash, semen, combinations, and the like. The volume of the sample utilized in accordance with the presently disclosed and/or claimed inventive concept(s) is from about 0.1 to about 100 microliters. As used herein, the term "volume" as it relates to the liquid test sample utilized in accordance with the presently disclosed and/or claimed inventive concept(s) means from about 0.1 microliter to about 100 microliters, or from about 1 microliter to about 75 microliters, or from about 2 microliters to about 60 microliters, or less than or equal to about 50 microliters, or less than or equal to about 40 microliters. In one non-limiting embodiment of the presently disclosed and/or claimed inventive concept(s), the liquid test sample is a patient's whole blood sample comprising and/or consisting of about 10 microliters to about 30 microliters in volume.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "plasma" refers to the liquid component of blood that is responsible for holding the blood cells in a whole blood sample in suspension that carries cells and proteins throughout the body. In one non-limiting embodiment, plasma may comprise and/or consist of dissolved proteins and/or analyte(s), such as, by way of example only, serum albumins, globulins, and fibrinogen, glucose, clotting factors, electrolytes, such as, by way of example only, sodium, calcium, magnesium, bicarbonate, chloride ions, hormones, carbon dioxide, and oxygen.

The term "reaction vessel" includes any device(s) capable of performing at least one diagnostic assay as described herein. The reaction vessel may perform the diagnostic assay(s) manually, but, in most instances, the reaction vessel will be inserted into a system that automates the performance of the diagnostic assay(s). In one non-limiting embodiment, the reaction vessel comprises a reaction cassette for use in automated diagnostic assays conducted by the DCA Vantage® Analyzer commercially available from Siemens Healthineers, Inc.

Turning now to particular embodiments, the presently disclosed and/or claimed inventive concept(s) relate to a device(s), kit(s), and method(s) for separating and metering a plasma sample from a patient's liquid test sample for the performance of one or more diagnostic assays.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radio-immunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and/or claimed inventive concept(s) are not strictly limited to immunoassays and may include, by way of example and not by limitation, chemical and chemical-based assays, nucleic acid assays, lipid-based assays, and serology-based assays. Immunoassays, including radioimmunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and/or claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any liquid test sample, including, without limitation, whole blood, plasma, serum, or urine.

Figure 1B:
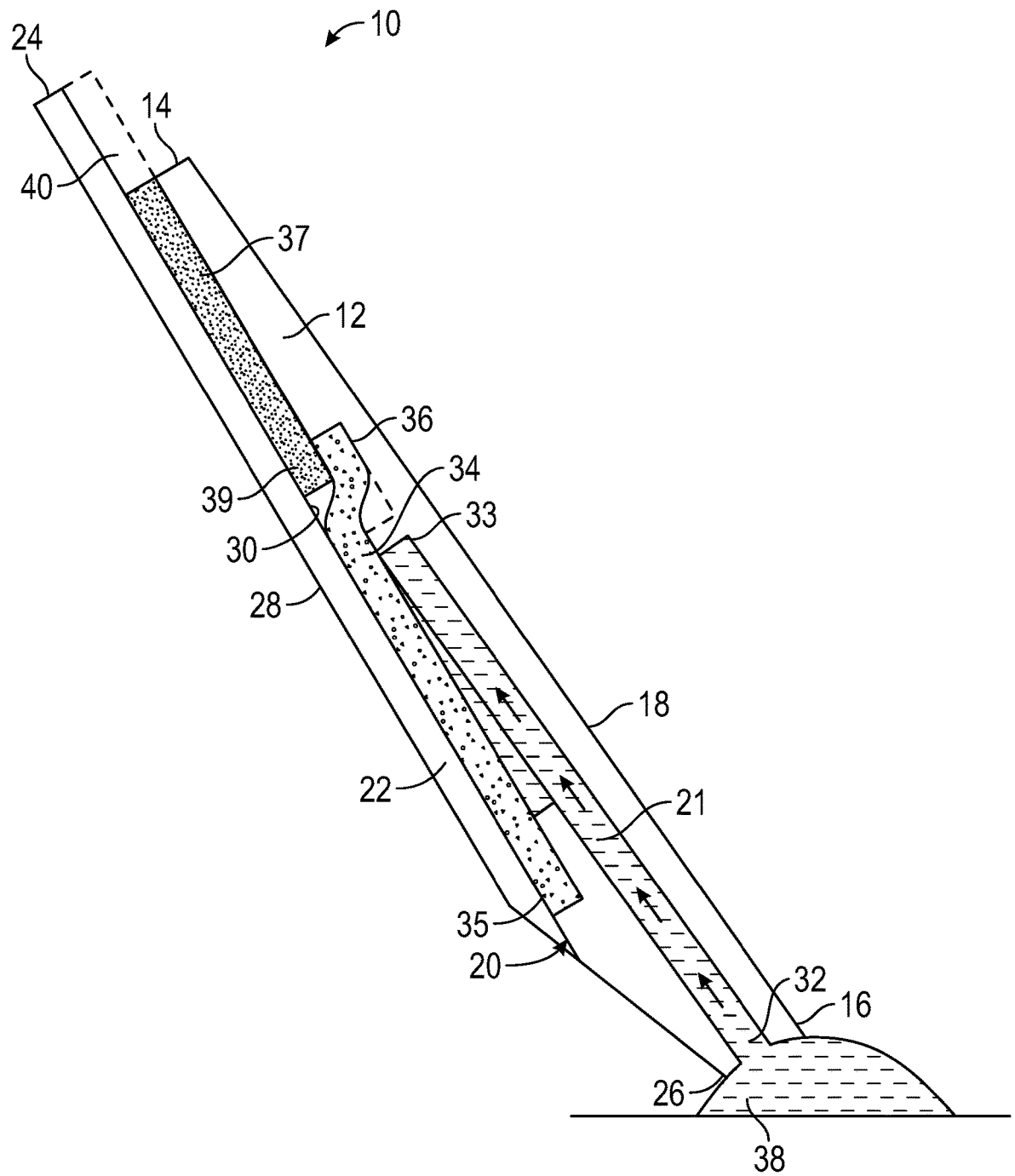
FIG. 1B is a side view of the improved sample device of FIG. 1A in which a patient's liquid test sample is collected within the improved sample device in accordance with the presently disclosed and/or claimed inventive concept(s).

Referring now to the Figures, and more particularly to FIGS. 1A-1B, shown therein is a non-limiting embodiment of an improved sample device 10 that is configured in a collection position for the collection of a patient's liquid test sample 38. In one non-limiting embodiment, the sample device 10 comprises and/or consists of a top portion 12, a bottom portion 22, at least one red blood cell capture membrane 34, and at least one plasma membrane 37.

In one non-limiting embodiment, and as shown in FIGS. 1A-1B, the top portion 12 comprises and/or consists of a first end 14, a second end 16, a top side 18, a bottom side 20, and a sample channel 21. Suitable materials for constructing the top portion 12, include, without limitation, synthetic and/or naturally-occurring or derived polymers (both organic and/or inorganic), such as, by way of example only, thermoplastic polymer(s), thermoset polymer(s), elastomer(s), and/or synthetic fiber(s) such as low-density polyethylene, high density polyethylene, polystyrene, polyvinylchloride, styrene butadiene, polyacrylics, polyvinyl acetate, and combinations thereof. The top portion 12 can be configured to be any shape capable of accomplishing the presently disclosed and/or claimed inventive concept(s), including, without limitation, circular, ovular, triangular, square, rectangular, trapezoidal, pentagonal, hexagonal, heptagonal, octagonal, nonagonal, decagonal, or polygonal.

In one non-limiting embodiment, the top portion 12 comprises a sample channel 21 that is adapted to collect a patient's liquid test sample 38, the sample channel 21 further comprising a first end 32 having an opening for receiving the patient's liquid test sample 38 and a second end 33, wherein at least a portion of the second end 33 is open to, in direct contact with, and/or in fluid communication with at least a portion of the red blood cell capture membrane 34 (discussed in greater detail hereinbelow). When the sample device 10 is in a collection position, the sample channel 21 collects the patient's liquid test sample 38 for instance, via capillary action, when the opening of the first end 32 of the sample channel 21 is in contact with the patient's liquid test sample 38. However, a person having ordinary skill in the art should readily appreciate that the patient's liquid test sample 38 can be collected by the sample channel 21 via any method commonly known in the art, including, without limitation, via creation of a negative pressure differential that draws the patient's liquid test sample 38 into the sample channel 21. The size and volume-capacity of the sample channel 21 will vary depending on the type and quantity of the patient's liquid test sample 38 being collected. In certain non-limiting embodiments, the sample channel 21 may be adapted and sized to hold volumes of from about 0.1 microliter to about 100 microliters, or from about 0.5 microliters to about 95 microliters, or from about 1 microliter to about 90 microliters, or from about 2 microliters to about 85 microliters, or from about 5 microliters to about 80 microliters, or from about 10 microliters to about 75 microliters, or from about 15 microliters to about 70 microliters, or from about 20 microliters to about 65 microliters, or from about 25 microliters to about 60 microliters, or from about 30 microliters to about 55 microliters, or from about 35 to about 50 microliters, or less than or equal to about 40 microliters. By way of example only, and not by way of limitation, the volume capacity of the sample channel 21 may comprise a volume of from about 10 microliters to about 20 microliters when the patient's liquid test sample 38 is whole blood. While shown in FIGS. 1A-1B as being formed within the top portion 12 of the sample device 10 (for instance, by way of example only, via injection molding), a person having ordinary skill in the art should readily appreciate that the sample channel 21 may be formed by the securement of the top portion 12 and the bottom portion 22 such that the sample channel 21 is defined by a portion of the bottom side 20 of the top portion 12 and a bottom side 30 of the bottom portion 22.

The sample device 10 further comprises and/or consists of the bottom portion 22, the bottom portion 22 comprising and/or consisting of a first end 24, a second end 26, a top side 28, and a bottom side 30. The bottom portion may be constructed from and shaped in any manner as previously described with respect to the top portion 12. As previously discussed, the sample channel 21 may be formed from the securement of the top portion 12 and the bottom portion 22 to one another via, by way of example only, adhesive(s) commonly known in the art and/or via welding. When the sample channel 21 is formed in this manner, an opening is formed at the first end 32 of the sample channel 21, wherein the opening is defined by the second end 16 of the top portion 12 and the second end 26 of the bottom portion 22.

Regardless of the manner in which the sample channel 21 is formed, the sample channel 21 extends longitudinally from the second end 16 of the top portion 12 and the second end 26 of the bottom portion 22 such that the sample channel 21 is substantially parallel in orientation to the top side 18 of the top portion 12 and the top side 28 of the bottom portion 22. In one non-limiting embodiment the distance from the first end 32 of the sample channel 21 to the second end 33 of the sample channel is about 1 centimeter, although a person having ordinary skill in the art should readily understand that the above-referenced distance of the sample channel 21 may be any distance capable of accomplishing the presently disclosed and/or claimed inventive concept(s). In one non-limiting embodiment, when the sample channel 21 is formed from the securement of the top portion 12 and bottom portion 22 to one another, the top portion 12 and bottom portion 22 are configured such that the sample channel 21 is capable of drawing in a patient's liquid test sample 38 through the opening of the first end 32 of the sample channel 21 via capillary action when the sample device 10 is placed in the collection position.

In one non-limiting embodiment, at least a portion of one wall forming the inside of the sample channel 21 may be coated or partially coated with at least one anticoagulant compound(s), including, without limitation, sodium heparin, lithium heparin, warfarin, rivaroxaban, dabigatran, apixaban, edoxaban, enoxaparin, fondaparinux, ethylenediaminetetraacetic acid (EDTA), and combinations thereof.

The sample device 10 further comprises and/or consists of at least one red blood cell capture membrane 34, the red blood cell capture membrane 34 comprising and/or consisting of a first end 35 and a second end 36. As previously described, in one non-limiting embodiment, a portion of the red blood cell capture membrane 34 at or near the second end 36 of the red blood cell capture membrane 34 is in direct contact with and/or in fluid communication with at least the second end 33 of the sample channel 21 such that the patient's liquid test sample 38 may be drawn into the red blood cell capture membrane 34 via, for instance, capillary action from the second end 33 of the sample channel 21. In addition, as shown in FIGS. 1A-1B, in one non-limiting embodiment, the red blood cell capture membrane is positioned and contained entirely between the top portion 12 and the bottom portion 22 of the sample device 10 and is configured in a substantially parallel orientation to the sample channel 21; however, a person having ordinary skill in the art should readily appreciate that the red blood cell capture membrane 34 may be oriented in any position capable of accomplishing the presently disclosed and/or claimed inventive concept(s). The red blood cell capture membrane 34 may be constructed of any material capable of substantially separating and retaining red blood cells from a patient's liquid test sample (i.e., a whole blood sample), while allowing the plasma to freely move through the red blood cell capture membrane 34 into the plasma membrane 37 (described in further detail hereinbelow). Suitable construction materials for the red blood cell capture membrane 34 include, but are not limited to, lectins, such as, by way of example only, concanavalin A, lentil lectin, potato lectin, snowdrop lectin, ricin, peanut agglutinin, jacalin, hairy vetch lectin, wheat germ agglutinin, elderberry lectin, *Maackia amurensis* hemoagglutinin, *Ulex europaeus* agglutinin, and *Aleuria aurantia* lectin, anti-human red blood cell antibodies, asymmetric polysulfone membrane(s), and combinations thereof. In one non-limiting embodiment, the red blood cell capture membrane 34 comprises and/or consists of a potato lectin bound cellulose membrane.

The red blood cell capture membrane 34 (and/or the plasma membrane 37) may further comprise and/or consist of at least one dye to facilitate the visual detection of when the patient's liquid test sample 38 within the red blood cell capture membrane 34 and/or the plasma membrane 37. Any dye(s) commonly known in the art may be used in accordance with the presently disclosed and/or claimed inventive concept(s).

The sample device 10 further comprises and/or consists of at least one plasma membrane 37, the plasma membrane 37 comprising and/or consisting of a first end 39 and a second end 40. In one non-limiting embodiment, and as shown in FIGS. 1A-1B, a portion of the plasma membrane 37 at or near the first end 39 of the plasma membrane 37 is in direct contact with at least the second end 36 of the red blood cell capture membrane 34 such that the patient's plasma sample (as the red blood cells within the patient's liquid test sample 38 are substantially retained within the red blood cell capture membrane 34) is drawn into the plasma membrane 37 via, for instance, capillary action or via gravitational flow from the second end 36 of the red blood cell capture membrane 34. As shown in FIGS. 1A-1B, a portion of the plasma membrane 37 is contained entirely between the top portion 12 and the bottom portion 22, for instance, at least the first end 39 of the plasma membrane 37 that is contact with the second 36 of the red blood cell capture membrane 34 is wholly contained between the top portion 12 and the bottom portion 22 of the sample device 10. However, a portion of the plasma membrane 37, including, for instance, that portion of the plasma membrane 37 comprising the second end 40, protrudes from and/or through the first end 14 of the top portion 12 such that the plasma membrane comprises an exposed portion (not numbered) that is not contained within or between the top portion 12 and the bottom portion 22. The exposed portion may be any dimension capable of accomplishing the presently disclosed and/or claimed inventive concept(s), including, without limitation, delivery of a patient's plasma sample 38 into a reaction channel 42 of a reaction vessel 41 for the conductance of one or more analyte(s) detection and/or diagnostic assays. In one non-limiting embodiment, the exposed portion may have an exposed surface area of about 20 square millimeters that holds a plasma sample of about 1 microliter for use in the one or more analyte(s) detection and/or diagnostic assays. In one non-limiting embodiment, once the exposed portion contains a pre-determined amount of a patient's plasma sample 46, the exposed portion of the plasma membrane 37 may be pinched, separated from, or cut off (either before or after the sample device 10 is placed in a reaction vessel 41) in order to meter and ensure that the exposed portion contains and delivers a predetermined volume of a patient's plasma sample into a reaction channel 42 for the conductance of at least one analyte(s) detection and/or diagnostic assays. In one non-limiting embodiment, the predetermined volume of the patient's plasma sample may comprise and/or consist of a volume of from about 0.5 microliters to about 20 microliters, or from about 1 microliter to about 15 microliters, or from about 1.5 microliters to about 10 microliters, or from about 2 microliters to about 9 microliters, or from about 3 microliters to about 8 microliters, or from about 4 microliters to about 7 microliters, or from about 5 microliters to about 6 microliters. In one non-limiting embodiment, the predetermined volume of the patient's plasma sample is about 1 microliter.

In one non-limiting embodiment, the plasma membrane 37 may comprise a length of from about 7 microns to about 15 microns.

The plasma membrane 37 may be constructed of any material(s) capable of accomplishing the presently disclosed and/or claimed inventive concept(s). Suitable materials for construction of the plasma membrane 37 include, but are not limited to, cellulose (with or without binder), nitrocellulose, carboxymethylcellulose, glass fiber, synthetic paper, and combinations thereof.

Figure 1C:
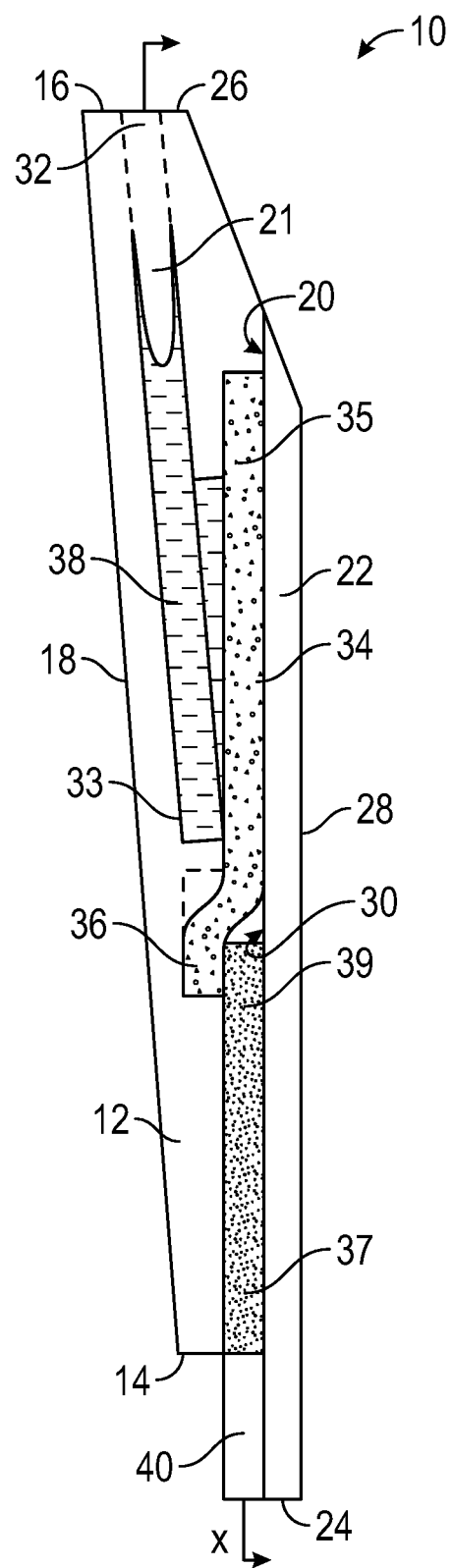
FIG. 1C is a side view of the improved sample device of FIG. 1B in which the patient's liquid test sample has been collected within the improved sample device which has been inverted into a sampling position in accordance with the presently disclosed and/or claimed inventive concept(s).

Referring now to FIG. 1C, following collection of the patient's liquid test sample (such as, by way of example, a patient's whole blood sample), the sample device 10 is then inverted into a sampling position for placement within a reaction vessel 41.

When placed in the sampling position (either before or after being placed within a reaction vessel 41), the patient's liquid test sample 38 contained within the sample channel 21 flows (for instance, via gravity and/or via capillary action) from at least a portion of the second end 33 of the sample channel 21 into the red blood cell capture membrane 34. As the patient's liquid test sample 38 contacts and enters into the red blood cell capture membrane 34, the patient's liquid test sample 38 flows through the red blood cell capture membrane 34. Accordingly, substantially all of the red blood cells present in the patient's liquid test sample 38 are captured by and retained within the red blood cell capture membrane 34 such that the sample that enters the plasma membrane 37 (for instance, from the second end 36 of the red blood cell capture membrane 34) primarily comprises and/or consists of plasma 46 (as shown in greater detail in FIG. 2), as well as any hemolyzed hemoglobin which may be contained therein). Once the plasma 46 enters into the plasma membrane 37 (for instance, into the first end 39 of the plasma membrane 37, the plasma 46 travels in and throughout the plasma membrane 37 such that any additional impurities and/or remaining whole red blood cells are removed from the plasma 46. In addition, the plasma membrane 37, both through its configuration and structure (for instance, controlling the flow of the plasma 46 via the pore size(s) of, by way of example, a nitrocellulose plasma membrane 46), allow for the accurate metering of the plasma 46 such that a predetermined volume of plasma 46 is delivered to and resides within the exposed portion near the second end 40 of the plasma membrane 37.

In one non-limiting embodiment, the exposed portion near the second end 40 of the plasma membrane comprises a surface area of about 20 square millimeters and the predetermined volume of plasma comprises about 1 microliter.

Figure 2:
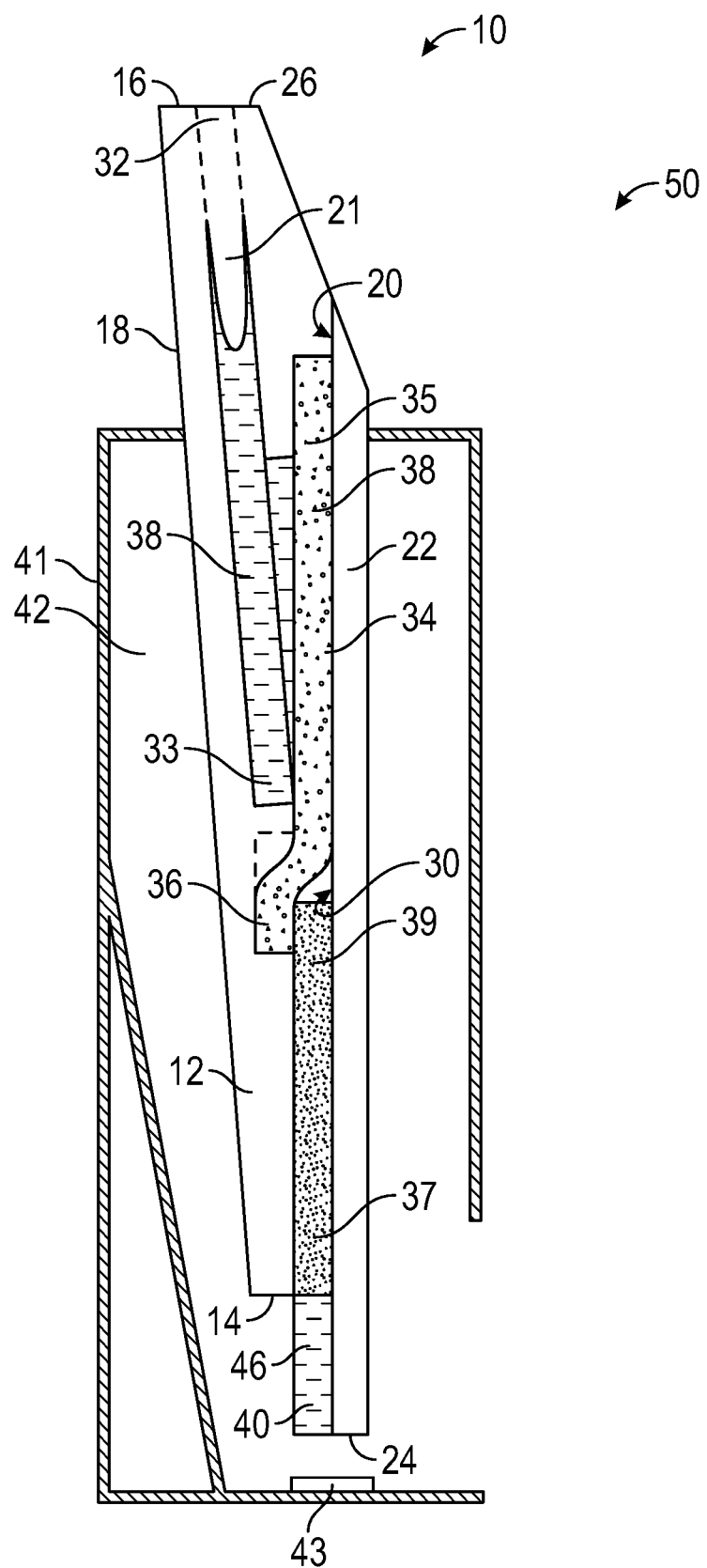
FIG. 2 is a side view of the improved sample device of FIG. 1C which has been positioned and secured within a reaction chamber of a reaction vessel in accordance with the presently disclosed and/or claimed inventive concept(s).

Referring now to FIG. 2, shown therein is the sample device 10 described in FIG. 1C which has been inserted in and secured within a reaction vessel 41 to form a diagnostic assay kit 50. The description of the sample device 10 with respect to FIG. 1C is deemed wholly applicable to the sample device 10 shown in FIG. 2 and, for purposes of brevity, shall not be reiterated herein.

Once secured within a reaction channel 42 of the reaction vessel 41, the predetermined volume (such as, by way for example only, about 1 microliter) of plasma 46 resides in and is contained within the exposed portion near the second end 40 of the plasma membrane 37. As previously described, the sample device 10 may be configured such that once the predetermined volume of plasma is delivered into the exposed portion, the exposed portion is pinched, closed off, and/or separated from the remainder of the plasma membrane 37 such that the predetermined volume of plasma 46 within the exposed portion remains accurate prior to and during the conductance of one or more analyte(s) detection and/or diagnostic assay(s) within the reaction channel 42 of the reaction vessel 41. Such pinching, closing, and/or separation of the exposed portion may occur prior to or during the insertion of the sample device 10 into the reaction vessel 41.

After securement within the reaction channel 42 of the reaction vessel 41, the exposed portion of the plasma membrane containing the predetermined volume of plasma 46 is then removed from the exposed portion by exposure to at least one liquid buffer and/or at least one liquid reagent (not shown), wherein the plasma sample 46 is mixed with the at least one buffer and/or at least one liquid reagent for the conductance of at least analyte(s) detection and/or diagnostic assay within the reaction chamber 42 of the reaction vessel 41. In addition, once mixed, the plasma 46 mixed with the buffer(s) and/or liquid reagent(s) may further associate and/or react with at least one solid reagent, for instance at least one solid reagent present on reagent pad 43, for the conductance of one or more analyte(s) detection and/or diagnostic assay(s), such as, for instance, an assay(s) for the detection of the presence of hemolyzed and/or glycated hemoglobin present within the plasma sample 46.

Figure 3:
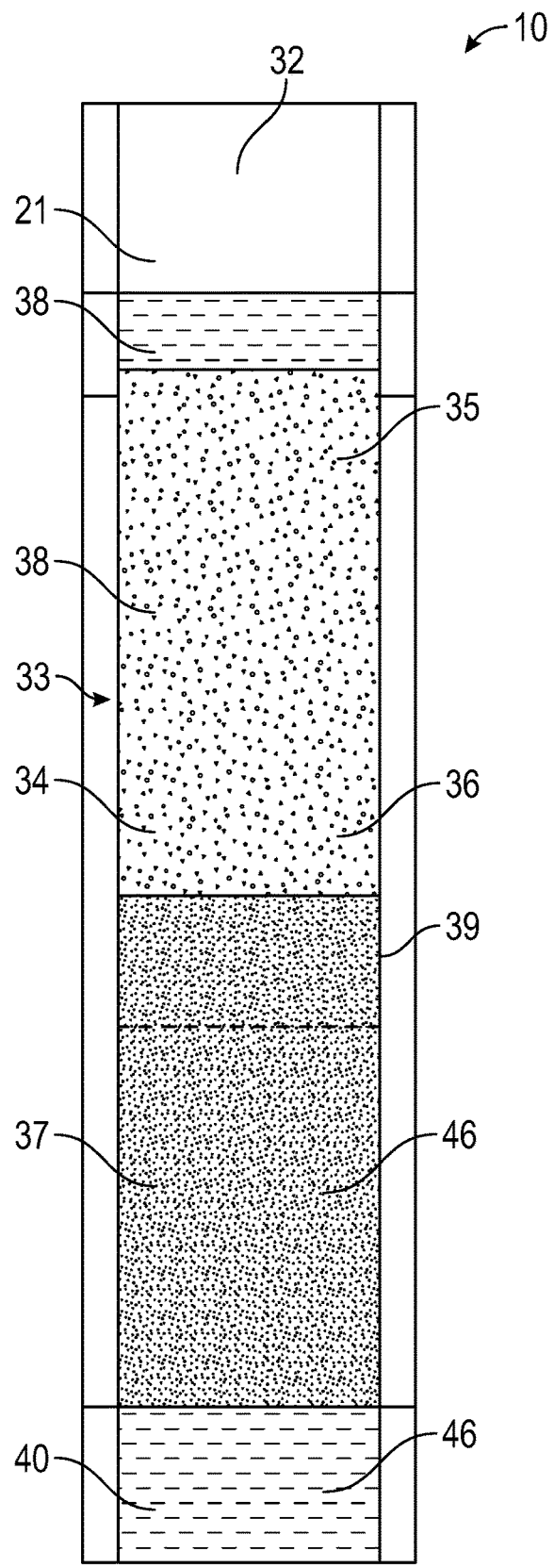
FIG. 3 is a cross-sectional view of the of the improved sample device of FIG. 2.

Referring now to FIG. 3, shown therein a cross-sectional view of the of the sample device 10 of FIG. 2 viewed from cross-sectional line x which depicts the flow of the patient's liquid test sample through the various components of the sample device 10.

NON-LIMITING ILLUSTRATIVE
EMBODIMENTS OF THE INVENTIVE
CONCEPT(S)

Illustrative embodiment 1. A sample device for separating and metering a plasma sample from a patient's liquid test sample for the performance of one or more diagnostic assay, comprising: a top portion, the top portion comprising a first end, a second end, a top side, a bottom side, and a sample channel disposed between the top side and bottom side and having a first opening at the second end for collecting a patient's liquid test sample, the sample channel extending longitudinally from the second end to the first end of the top portion, wherein the first end has a second opening; a bottom portion, the bottom portion comprising a first end, a second end, a top side, and a bottom side, wherein the bottom portion is secured to the top portion; at least one red blood cell capture membrane, the at least one red blood cell capture membrane comprising a first end and a second end, wherein the second end of the red blood cell capture membrane is in substantially direct contact with the second opening of the first end of the top portion; and at least one plasma membrane, the at least one plasma membrane comprising a first end and a second end.

Illustrative embodiment 2. The sample device of illustrative embodiment 1, wherein the first end of the plasma membrane is in substantially direct contact (or fluid communication) with the second end of the at least one red blood cell capture membrane.

Illustrative embodiment 3. The sample device of illustrative embodiment 1 or 2, wherein the patient's liquid test sample comprises a volume of whole blood.

Illustrative embodiment 4. The sample device of illustrative embodiment 3, wherein the volume of whole blood is from about 10 microliters to about 30 microliters.

Illustrative embodiment 5. The sample device of any of illustrative embodiments 1-4, wherein the diagnostic assay is at least one analyte detection assay for the detection of at least one analyte selected from the group consisting of IgG, IgG CSF, IgG subclasses 1-4, IgA, IgM, Ig/light chain, type kappa, Ig/light chain, type lambda, FLC kappa, FLC lambda, β2-microglobulin, albumin urine, α1-microglobulin urine, α2-microglobulin, β2-microglobulin urine, cystatin C (serum), IgG urine, Ig/light chain, type kappa urine, Ig/light chain, type lambda urine, transferrin urine, α1-acid glycoprotein, C-reactive protein (CRP), fibrinogen, serum amyloid A (SAA), ADNase B, arginosuccinate lyase (ASL), rheumatoid factor (RF), complement C3 protein (C3c), complement C4 protein (C4), high sensitivity CRP, apolipoprotein A-1 (apo A-1), apolipoprotein B (apo B), homocysteine, lipoprotein (a) (Lp(a)), myoglobin, cystatin C, carbohydrate deficient transferrin (CDT), transferrin, IgE, albumin, prealbumin, retinol binding protein (RBP), ferritin, antithrombin III protein (AT-III), plasminogen, haptoglobin, hemopexin, soluble transferrin receptor protein (sTfR), C1 esterase inhibitor, albumin CSF, IgA CSF, IgM CSF, α1-antitrypsin, α2-macroglobulin, apolipoprotein A-II, apolipoprotein E, ceruloplasmin, fibronectin, folate, vitamin B12, vitamin D, brain natriuretic peptide (BNP), creatine kinase-MB (CKMB), high sensitivity troponin I (TNIH), N-terminal pro b-type natriuretic peptide (NT-proBNP), troponin I, microalbumin, 6-acetylmorphine (6-AM), acetaminophen, amphetamines, barbiturates, benzodiazepines, caffeine, cannabinoids, cocaine metabolite(s), ecstasy, ethyl alcohol, methadone, methaqualone, opiates, phencyclidine, propoxyphene, salicylate, tricyclic antidepressants, cyclosporine, mycophenolic acid, sirolimus, tacrolimus, prostate-specific antigen (PSA), human chorionic gonadotropin (hCG), amikacin, carbamazepine, digitoxin, digoxin, gabapentin, gentamicin, lamotrigine, levetiracetam, lidocaine, lithium, methotrexate, N-acetylprocainamide (NAPA), phenobarbital, phenytoin, procainamide, theophylline, tobramycin, topiramate, valproic acid, vancomycin, zonisamide, triiodothyronine (T3), thyroxine (T4), thyroid hormone uptake, thyroid-stimulating hormone (TSH), and combinations thereof.

Illustrative embodiment 6. The sample device of any of illustrative embodiments 1-5, wherein the top portion and bottom portion are constructed from materials selected from the group consisting of low-density polyethylene, high density polyethylene, polystyrene, polyvinylchloride, styrene butadiene, polyacrylics, polyvinyl acetate, and combinations thereof.

Illustrative embodiment 7. The sample device of any of illustrative embodiments 1-6, wherein the at least one red blood cell capture membrane is entirely contained between the top portion and bottom portion of the sample device.

Illustrative embodiment 8. The sample device of any of illustrative embodiments 1-7, wherein the second end of the at least one plasma membrane is located outside of the top portion and bottom portion of the sample device.

Illustrative embodiment 9. The sample device of any of illustrative embodiments 1-8, wherein the at least one red blood cell capture device is constructed of materials selected from the group consisting of concanavalin A, lentil lectin, potato lectin, snowdrop lectin, ricin, peanut agglutinin, jacalin, hairy vetch lectin, wheat germ agglutinin, elderberry lectin, *Maackia amurensis* hemoagglutinin, *Ulex europaeus* agglutinin, *Aleuria aurantia* lectin, anti-human red blood cell antibodies, asymmetric polysulfone membrane(s), and combinations thereof.

Illustrative embodiment 10. The sample device of any of illustrative embodiments 1-9, wherein the at least one plasma membrane is constructed of materials selected from the group consisting of cellulose with binder, cellulose without binder, nitrocellulose, carboxymethylcellulose, glass fiber, synthetic paper, and combinations thereof.

Illustrative embodiment 11. The sample device of any of illustrative embodiments 1-10, wherein at least a portion of the sample channel is at least partially coated with at least one anticoagulant compound.

Illustrative embodiment 12. The sample device of illustrative embodiment 11, wherein the at least one anticoagulant compound is selected from the group consisting of sodium heparin, lithium heparin, warfarin, rivaroxaban, dabigatran, apixaban, edoxaban, enoxaparin, fondaparinux, ethylenediaminetetraacetic acid (EDTA), and combinations thereof.

Illustrative embodiment 13. The sample device of any of illustrative embodiments 1-12, wherein the patient's liquid test sample is collected by and transferred through the sample device via capillary action.

Illustrative embodiment 14. A method of separating and metering a plasma sample from a patient's liquid test sample for use within at least one diagnostic assay, the method comprising the steps of: collecting a patient's liquid test sample into a sample device, the sample device comprising: a top portion, the top portion comprising a first end, a second end, a top side, a bottom side, and a sample channel disposed between the top side and bottom side and having a first opening at the second end for collecting the patient's liquid test sample, the sample channel extending longitudinally from the second end to the first end of the top portion, wherein the first end has a second opening; a bottom portion, the bottom portion comprising a first end, a second end, a top side, and a bottom side, wherein the bottom portion is secured to the top portion; at least one red blood cell capture membrane, the at least one red blood cell capture membrane comprising a first end and a second end, wherein the second end of the red blood cell capture membrane is in substantially direct contact with the second opening of the first end of the top portion; and at least one plasma membrane, the at least one plasma membrane comprising a first end and a second end; transferring the patient's liquid test sample from the sample channel into the at least one red blood cell capture membrane such that any red blood cells contained within the patient's liquid test sample are separated and retained within the at least one red blood cell capture membrane, thereby forming a plasma sample; transferring the plasma sample from the at least one red blood cell capture membrane into the at least one plasma membrane such that a predetermined volume of the plasma sample resides and is substantially contained within the second end of the at least one plasma membrane for use in at least one diagnostic assay.

Illustrative embodiment 15. The method of illustrative embodiment 14, wherein the patient's liquid test sample comprises a volume of whole blood.

Illustrative embodiment 16. The method of illustrative embodiment 15, wherein the volume of whole blood is from about 10 microliters to about 30 microliters.

Illustrative embodiment 17. The method of any of illustrative embodiments 14-16, wherein the first end of the plasma membrane is in substantially direct contact with the second end of the at least one red blood cell capture membrane.

Illustrative embodiment 18. The method of any of illustrative embodiments 14-17, wherein the diagnostic assay is at least one analyte detection assay for the detection of at least one analyte selected from the group consisting of IgG, IgG CSF, IgG subclasses 1-4, IgA, IgM, Ig/light chain, type kappa, Ig/light chain, type lambda, FLC kappa, FLC lambda, β2-microglobulin, albumin urine, α1-microglobulin urine, α2-microglobulin, β2-microglobulin urine, cystatin C (serum), IgG urine, Ig/light chain, type kappa urine, Ig/light chain, type lambda urine, transferrin urine, α1-acid glycoprotein, C-reactive protein (CRP), fibrinogen, serum amyloid A (SAA), ADNase B, arginosuccinate lyase (ASL), rheumatoid factor (RF), complement C3 protein (C3c), complement C4 protein (C4), high sensitivity CRP, apolipoprotein A-1 (apo A-1), apolipoprotein B (apo B), homocysteine, lipoprotein (a) (Lp(a)), myoglobin, cystatin C, carbohydrate deficient transferrin (CDT), transferrin, IgE, albumin, prealbumin, retinol binding protein (RBP), ferritin, antithrombin III protein (AT-Ill), plasminogen, haptoglobin, hemopexin, soluble transferrin receptor protein (sTfR), C1 esterase inhibitor, albumin CSF, IgA CSF, IgM CSF, a1-antitrypsin, α2-macroglobulin, apolipoprotein A-II, apolipoprotein E, ceruloplasmin, fibronectin, folate, vitamin B12, vitamin D, brain natriuretic peptide (BNP), creatine kinase-MB (CKMB), high sensitivity troponin I (TNIH), N-terminal pro b-type natriuretic peptide (NT-proBNP), troponin I, microalbumin, 6-acetylmorphine (6-AM), acetaminophen, amphetamines, barbiturates, benzodiazepines, caffeine, cannabinoids, cocaine metabolite(s), ecstasy, ethyl alcohol, methadone, methaqualone, opiates, phencyclidine, propoxyphene, salicylate, tricyclic antidepressants, cyclosporine, mycophenolic acid, sirolimus, tacrolimus, prostate-specific antigen (PSA), human chorionic gonadotropin (hCG), amikacin, carbamazepine, digitoxin, digoxin, gabapentin, gentamicin, lamotrigine, levetiracetam, lidocaine, lithium, methotrexate, N-acetylprocainamide (NAPA), phenobarbital, phenytoin, procainamide, theophylline, tobramycin, topiramate, valproic acid, vancomycin, zonisamide, triiodothyronine (T3), thyroxine (T4), thyroid hormone uptake, thyroid-stimulating hormone (TSH), and combinations thereof.

Illustrative embodiment 19. The method of any of illustrative embodiments 14-18, wherein the top portion and bottom portion are constructed from materials selected from the group consisting of low-density polyethylene, high density polyethylene, polystyrene, polyvinylchloride, styrene butadiene, polyacrylics, polyvinyl acetate, and combinations thereof.

Illustrative embodiment 20. The method of any of illustrative embodiments 14-19, wherein the at least one red blood cell capture membrane is entirely contained between the top portion and bottom portion of the sample device.

Illustrative embodiment 21. The method of any of illustrative embodiments 14-20, wherein the second end of the at least one plasma membrane is located outside of the top portion and bottom portion of the sample device.

Illustrative embodiment 22. The method of any of illustrative embodiments 14-21, wherein the at least one red blood cell capture device is constructed of materials selected from the group consisting of concanavalin A, lentil lectin, potato lectin, snowdrop lectin, ricin, peanut agglutinin, jacalin, hairy vetch lectin, wheat germ agglutinin, elderberry lectin, *Maackia amurensis* hemoagglutinin, *Ulex europaeus* agglutinin, *Aleuria aurantia* lectin, anti-human red blood cell antibodies, asymmetric polysulfone membrane(s), and combinations thereof.

Illustrative embodiment 23. The method of any of illustrative embodiments 14-22, wherein the at least one plasma membrane is constructed of materials selected from the group consisting of cellulose with binder, cellulose without binder, nitrocellulose, carboxymethylcellulose, glass fiber, synthetic paper, and combinations thereof.

Illustrative embodiment 24. The method of any of illustrative embodiments 14-23, wherein at least a portion of the sample channel is at least partially coated with at least one anticoagulant compound.

Illustrative embodiment 25. The method of illustrative embodiment 24, wherein the at least one anticoagulant compound is selected from the group consisting of sodium heparin, lithium heparin, warfarin, rivaroxaban, dabigatran, apixaban, edoxaban, enoxaparin, fondaparinux, ethylenediaminetetraacetic acid (EDTA), and combinations thereof.

Illustrative embodiment 26. The method of any of illustrative embodiments 14-25, wherein the patient's liquid test sample is collected by and transferred through the sample device via capillary action.

Thus, in accordance with the presently disclosed and/or claimed inventive concept(s), there have been provided devices, kits, and methods for at least one liquid test sample within a reaction vessel for use in analyte(s) detection/diagnostic assays. As described herein, the presently disclosed and/or claimed inventive concept(s) relate to embodiments of an improved plasma separation and sample metering device that is able to separate and a patient's extracted plasma sample for use in at least one analyte(s) detection and/or diagnostic assay. Such presently disclosed and/or claimed inventive concept(s) fully satisfy the objectives and advantages set forth hereinabove. Although the presently disclosed and/or claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and/or claimed inventive concept(s).

What is claimed is:

1. A method of separating and metering a plasma sample from a patient's liquid test sample for use within at least one diagnostic assay, the method comprising the steps of:

collecting a patient's liquid test sample into a sample device, the sample device comprising:
- a top portion, the top portion comprising a first end, a second end, a top side, a bottom side, and a sample channel disposed between the top side and bottom side and having a first opening at the second end for collecting the patient's liquid test sample, the sample channel extending longitudinally from the second end to the first end of the top portion, wherein the first end has a second opening;
- a bottom portion, the bottom portion comprising a first end, a second end, a top side, and a bottom side, wherein the bottom portion is secured to the top portion;
- at least one red blood cell capture membrane, the at least one red blood cell capture membrane comprising a first end and a second end, wherein the second end of the red blood cell capture membrane is in substantially direct contact with the second opening of the sample channel; and
- at least one plasma membrane comprising a first end and a second end, wherein the plasma membrane is configured and structured to hold a specific volume of plasma, wherein the first end of the plasma membrane is in substantially direct contact with the second end of the at least one red blood cell capture membrane, wherein the second end of the plasma membrane extends beyond the first end of the top portion thereby forming an exposed portion of the plasma membrane, wherein the exposed portion of the plasma membrane has a surface area that holds a predetermined volume of plasma, and wherein the exposed portion of the plasma membrane is isolatable from the remainder of the plasma membrane to meter and deliver a predetermined volume of patient plasma for performance of the one or more diagnostic assays;

transferring the patient's liquid test sample from the sample channel into the at least one red blood cell capture membrane such that any red blood cells contained within the patient's liquid test sample are separated and retained within the at least one red blood cell capture membrane, thereby forming a plasma sample;

allowing the plasma sample to flow from the at least one red blood cell capture membrane into the at least one plasma membrane whereby the plasma membrane is filled with the specific volume of plasma such that a predetermined volume of the plasma sample resides and is substantially contained within the exposed portion of the plasma membrane; and pinching, separating, or cutting off the exposed portion of the plasma membrane to isolate the predetermined volume of the plasma sample for use in at least one diagnostic assay.

2. The method of claim 1, wherein the patient's liquid test sample comprises a volume of whole blood.

3. The method of claim 2, wherein the volume of whole blood is from about 10 microliters to about 30 microliters.

4. The method of claim 1, wherein the diagnostic assay is at least one analyte detection assay for the detection of at least one analyte selected from the group consisting of IgG, IgG CSF, IgG subclasses 1-4, IgA, IgM, Ig/light chain, type kappa, Ig/light chain, type lambda, FLC kappa, FLC lambda, β2-microglobulin, albumin urine, α1-microglobulin urine, α2-microglobulin, β2-microglobulin urine, cystatin C (serum), IgG urine, Ig/light chain, type kappa urine, Ig/light chain, type lambda urine, transferrin urine, α1-acid glycoprotein, C-reactive protein (CRP), fibrinogen, serum amyloid A (SAA), ADNase B, arginosuccinate lyase (ASL), rheumatoid factor (RF), complement C3 protein (C3c), complement C4 protein (C4), high sensitivity CRP, apolipoprotein A-1 (apo A-1), apolipoprotein B (apo B), homocysteine, lipoprotein (a) (Lp(a)), myoglobin, cystatin C, carbohydrate deficient transferrin (CDT), transferrin, IgE, albumin, prealbumin, retinol binding protein (RBP), ferritin, antithrombin III protein (AT-III), plasminogen, haptoglobin, hemopexin, soluble transferrin receptor protein (sTfR), C1 esterase inhibitor, albumin CSF, IgA CSF, IgM CSF, α1-antitrypsin, α2-macroglobulin, apolipoprotein A-II, apolipoprotein E, ceruloplasmin, fibronectin, folate, vitamin B12, vitamin D, brain natriuretic peptide (BNP), creatine kinase-MB (CKMB), high sensitivity troponin I (TNIH), N-terminal pro b-type natriuretic peptide (NT-proBNP), troponin I, microalbumin, 6-acetylmorphine (6-AM), acetaminophen, amphetamines, barbiturates, benzodiazepines, caffeine, cannabinoids, cocaine metabolite(s), ecstasy, ethyl alcohol, methadone, methaqualone, opiates, phencyclidine, propoxyphene, salicylate, tricyclic antidepressants, cyclosporine, mycophenolic acid, sirolimus, tacrolimus, prostate-specific antigen (PSA), human chorionic gonadotropin (hCG), amikacin, carbamazepine, digitoxin, digoxin, gabapentin, gentamicin, lamotrigine, levetiracetam, lidocaine, lithium, methotrexate, N-acetylprocainamide (NAPA), phenobarbital, phenytoin, procainamide, theophylline, tobramycin, topiramate, valproic acid, vancomycin, zonisamide, triiodothyronine (T3), thyroxine (T4), thyroid hormone uptake, thyroid-stimulating hormone (TSH), and combinations thereof.

5. The method of claim 1, wherein the top portion and bottom portion are constructed from materials selected from the group consisting of low-density polyethylene, high density polyethylene, polystyrene, polyvinylchloride, styrene butadiene, polyacrylics, polyvinyl acetate, and combinations thereof.

6. The method of claim 1, wherein the at least one red blood cell capture membrane is entirely contained between the top portion and bottom portion of the sample device.

7. The method of claim 1, wherein the second end of the at least one plasma membrane is located outside of the top portion and bottom portion of the sample device.

8. The method of claim 1, wherein the at least one red blood cell capture membrane comprises at least one substance selected from the group consisting of concanavalin A, lentil lectin, potato lectin, snowdrop lectin, ricin, peanut agglutinin, jacalin, hairy vetch lectin, wheat germ agglutinin, elderberry lectin, *Maackia amurensis* hemoagglutinin, *Ulex europaeus* agglutinin, *Aleuria aurantia* lectin, anti-human red blood cell antibodies, asymmetric polysulfone membrane(s), and combinations thereof.

9. The method of claim 1, wherein the at least one plasma membrane is constructed of materials selected from the group consisting of cellulose with binder, cellulose without binder, nitrocellulose, carboxymethylcellulose, glass fiber, synthetic paper, and combinations thereof.

10. The method of claim 1, wherein at least a portion of the sample channel is at least partially coated with at least one anticoagulant compound.

11. The method of claim 10, wherein the at least one anticoagulant compound is selected from the group consisting of sodium heparin, lithium heparin, warfarin, rivaroxaban, dabigatran, apixaban, edoxaban, enoxaparin, fondaparinux, ethylenediaminetetraacetic acid (EDTA), and combinations thereof.

12. The method of claim 1, wherein the patient's liquid test sample is collected by and transferred through the sample device via capillary action.

13. The method of claim 1, further comprising the step of removing the predetermined volume of plasma from the isolated exposed portion of the plasma membrane by exposing the isolated exposed portion of the plasma membrane to at least one liquid buffer and/or reagent.

14. The method of claim 1, wherein the step of isolating the exposed portion of the plasma membrane is further defined as severing the exposed portion of the plasma membrane from the remainder of the plasma membrane.

15. The method of claim 1, wherein the step of allowing the plasma sample to flow from the at least one red blood cell capture membrane into the at least one plasma membrane comprises inverting the sample device into a sampling position.

16. A sample device for separating and metering a plasma sample from a patient's liquid test sample for the performance of one or more diagnostic assays, comprising:
 a top portion, the top portion comprising a first end, a second end, a top side, a bottom side, and a sample channel disposed between the top side and bottom side and having a first opening at the second end for collecting a patient's liquid test sample, the sample channel extending longitudinally from the second end to the first end of the top portion, wherein the first end has a second opening;
 a bottom portion, the bottom portion comprising a first end, a second end, a top side, and a bottom side, wherein the bottom portion is secured to the top portion;
 at least one red blood cell capture membrane, the at least one red blood cell capture membrane comprising a first end and a second end, wherein the second end of the red blood cell capture membrane is in substantially direct contact with the second opening of the sample channel, and wherein the at least one red blood cell capture membrane comprises at least one substance selected from the group consisting of concanavalin A, lentil lectin, potato lectin, snowdrop lectin, ricin, peanut agglutinin, jacalin, hairy vetch lectin, wheat germ agglutinin, elderberry lectin, maackia amurensis hemoagglutinin, ulex europaeus agglutinin, aleuria aurantia lectin, anti-human red blood cell antibodies, asymmetric polysulfone membrane(s), and combinations thereof;
 at least one plasma membrane comprising a first end and a second end, wherein the plasma membrane is configured and structured to hold a specific volume of plasma, wherein the first end of the plasma membrane is in substantially direct contact with the second end of the at least one red blood cell capture membrane, wherein the second end of the plasma membrane extends beyond the first end of the top portion thereby forming an exposed portion of the plasma membrane, and wherein the exposed portion of the plasma membrane has a surface area that holds a predetermined volume of plasma, and wherein once the predetermined volume of plasma is delivered into the exposed portion of the plasma membrane, the exposed portion is pinched, separated, or cut off from the remainder of the plasma membrane to meter and deliver the predetermined volume of patient plasma for performance of the one or more diagnostic assays.

17. The sample device of claim 16, wherein the patient's liquid test sample comprises a volume of whole blood.

18. The sample device of claim 17, wherein the volume of whole blood is from about 10 microliters to about 30 microliters.

19. The sample device of claim 16, wherein the diagnostic assay is at least one analyte detection assay for the detection of at least one analyte selected from the group consisting of IgG, IgG CSF, IgG subclasses 1-4, IgA, IgM, Ig/light chain, type kappa, Ig/light chain, type lambda, FLC kappa, FLC lambda, (32-microglobulin, albumin urine, a1-microglobulin urine, a2-microglobulin, (32-microglobulin urine, cystatin C (serum), IgG urine, Ig/light chain, type kappa urine, Ig/light chain, type lambda urine, transferrin urine, a1-acid glycoprotein, C-reactive protein (CRP), fibrinogen, serum amyloid A (SAA), ADNase B, arginosuccinate lyase (ASL), rheumatoid factor (RF), complement C3 protein (C3c), complement C4 protein (C4), high sensitivity CRP, apolipoprotein A-1 (apo A-1), apolipoprotein B (apo B), homocysteine, lipoprotein (a) (Lp(a)), myoglobin, cystatin C, carbohydrate deficient transferrin (CDT), transferrin, IgE, albumin, prealbumin, retinol binding protein (RBP), ferritin, antithrombin III protein (AT-Ill), plasminogen, haptoglobin, hemopexin, soluble transferrin receptor protein (sTfR), Cl esterase inhibitor, albumin CSF, IgA CSF, IgM CSF, al-antitrypsin, a2-macroglobulin, apolipoprotein A-II, apolipoprotein E, ceruloplasmin, fibronectin, folate, vitamin B12, vitamin D, brain natriuretic peptide (BNP), creatine kinase-MB (CKMB), high sensitivity troponin I (TNIH), N-terminal pro b-type natriuretic peptide (NT-proBNP), troponin I, microalbumin, 6-acetylmorphine (6-AM), acetaminophen, amphetamines, barbiturates, benzodiazepines, caffeine, cannabinoids, cocaine metabolite(s), ecstasy, ethyl alcohol, methadone, methaqualone, opiates, phencyclidine, propoxyphene, salicylate, tricyclic antidepressants, cyclosporine, mycophenolic acid, sirolimus, tacrolimus, prostate-specific antigen (PSA), human chorionic gonadotropin (hCG), amikacin, carbamazepine, digitoxin, digoxin, gabapentin, gentamicin, lamotrigine, levetiracetam, lidocaine, lithium, methotrexate, N-acetylprocainamide (NAPA), phenobarbital, phenytoin, procainamide, theophylline, tobramycin, topiramate, valproic acid, vancomycin, zonisamide, triiodothyronine (T3), thyroxine (T4), thyroid hormone uptake, thyroid-stimulating hormone (TSH), and combinations thereof.

20. The sample device of claim 16, wherein each of the top portion and bottom portion is constructed from materials selected from the group consisting of low-density polyethylene, high density polyethylene, polystyrene, polyvinylchloride, styrene butadiene, polyacrylics, polyvinyl acetate, and combinations thereof.

21. The sample device of claim 16, wherein the at least one red blood cell capture membrane is entirely contained between the top portion and bottom portion of the sample device.

22. The sample device of claim 16, wherein the second end of the at least one plasma membrane is located outside of the top portion and bottom portion of the sample device.

23. The sample device of claim 16, wherein the at least one plasma membrane is constructed of materials selected from the group consisting of cellulose with binder, cellulose without binder, nitrocellulose, carboxymethylcellulose, glass fiber, synthetic paper, and combinations thereof.

24. The sample device of claim 16, wherein at least a portion of the sample channel is at least partially coated with at least one anticoagulant compound.

25. The sample device of claim 24, wherein the at least one anticoagulant compound is selected from the group consisting of sodium heparin, lithium heparin, warfarin, rivaroxaban, dabigatran, apixaban, edoxaban, enoxaparin, fondaparinux, ethylenediaminetetraacetic acid (EDTA), and combinations thereof.

26. The sample device of claim 16, wherein the patient's liquid test sample is collected by and transferred through the sample device via capillary action.

27. The sample device of claim 16, wherein the exposed portion of the plasma membrane is severable from the remainder of the plasma membrane.

28. A sample device for separating and metering a plasma sample from a patient's liquid test sample for the performance of one or more diagnostic assays, comprising:
 a top portion, the top portion comprising a first end, a second end, a top side, a bottom side, and a sample channel disposed between the top side and bottom side and having a first opening at the second end for collecting a patient's liquid test sample, the sample channel extending longitudinally from the second end to the first end of the top portion, wherein the first end has a second opening, and wherein at least a portion of the sample channel is at least partially coated with at least one anticoagulant compound;
 a bottom portion, the bottom portion comprising a first end, a second end, a top side, and a bottom side, wherein the bottom portion is secured to the top portion;
 at least one red blood cell capture membrane, the at least one red blood cell capture membrane comprising a first end and a second end, wherein the second end of the red blood cell capture membrane is in substantially direct contact with the second opening of the sample channel;
 at least one plasma membrane comprising a first end and a second end, wherein the plasma membrane is configured and structured to hold a specific volume of plasma, wherein the first end of the plasma membrane is in substantially direct contact with the second end of the at least one red blood cell capture membrane, wherein the second end of the plasma membrane extends beyond the first end of the top portion thereby forming an exposed portion of the plasma membrane, and wherein the exposed portion of the plasma membrane has a surface area that holds a predetermined volume of plasma, and wherein once the predetermined volume of plasma is delivered into the exposed portion of the plasma membrane, the exposed portion is pinched, separated, or cut off from the remainder of the plasma membrane to meter and deliver the predetermined volume of patient plasma for performance of the one or more diagnostic assays.

29. The sample device of claim 24, wherein the at least one anticoagulant compound is selected from the group consisting of sodium heparin, lithium heparin, warfarin, rivaroxaban, dabigatran, apixaban, edoxaban, enoxaparin, fondaparinux, ethylenediaminetetraacetic acid (EDTA), and combinations thereof.

\* \* \* \* \*